United States Patent [19]
Feingold

[11] Patent Number: 6,083,236
[45] Date of Patent: Jul. 4, 2000

[54] KERATOME METHOD AND APPARATUS

[76] Inventor: Vladimir Feingold, 31732 Isle Vista, Laguna Niguel, Calif. 92677

[21] Appl. No.: 09/132,987

[22] Filed: Aug. 12, 1998

[51] Int. Cl.$^7$ ......................................................... A61F 9/00
[52] U.S. Cl. ................................................................ 606/166
[58] Field of Search ..................................... 606/166, 169

[56] References Cited

U.S. PATENT DOCUMENTS

| | | |
|---|---|---|
| Re. 35,421 | 1/1997 | Ruiz et al. . |
| 4,662,370 | 5/1987 | Hoffmann et al. . |
| 4,903,695 | 2/1990 | Warner et al. . |
| 5,063,942 | 11/1991 | Kilmer et al. . |
| 5,133,726 | 7/1992 | Ruiz et al. . |
| 5,288,292 | 2/1994 | Giraud et al. . |
| 5,318,044 | 6/1994 | Kilmer et al. . |
| 5,318,046 | 6/1994 | Rozakis . |
| 5,342,378 | 8/1994 | Giraud et al. . |
| 5,368,604 | 11/1994 | Kilmer et al. . |
| 5,395,385 | 3/1995 | Kilmer et al. . |
| 5,496,339 | 3/1996 | Koepnick . |
| 5,527,328 | 6/1996 | Pintucci . |
| 5,556,406 | 9/1996 | Gordon et al. . |
| 5,586,980 | 12/1996 | Kremer et al. . |
| 5,595,570 | 1/1997 | Smith . |
| 5,624,456 | 4/1997 | Hellenkamp . |
| 5,658,303 | 8/1997 | Koepnick . |
| 5,690,657 | 11/1997 | Koepnick ................................ 606/166 |

FOREIGN PATENT DOCUMENTS

| | | |
|---|---|---|
| 2 595 243 | 9/1987 | France . |
| 197 46 038 A1 | 4/1998 | Germany . |
| WO 90/01905 | 3/1990 | WIPO . |

*Primary Examiner*—Michael Buiz
*Assistant Examiner*—Vy Q. Bui
*Attorney, Agent, or Firm*—Ladas & Parry

[57] ABSTRACT

A keratome for performing corneal resectioning. The keratome has a positioning ring to position an eyeball with the cornea protruding through the ring to be restrained by an applanation shoe surface, which may be pivoted away. A blade is suspended from its ends by a blade support which is driven by a drive mechanism, so that the blade describes a forward path between the positioning ring and the applanation shoe at a controlled distance from the applanation shoe reference surface while also oscillating laterally, and preferably without the blade or the blade support touching either the positioning ring or the applanation shoe. A guide may be disposed parallel to the blade edge to control resectioning thickness. Drive control and vacuum for the positioning ring are provided under user command by a control unit having user inputs.

35 Claims, 13 Drawing Sheets

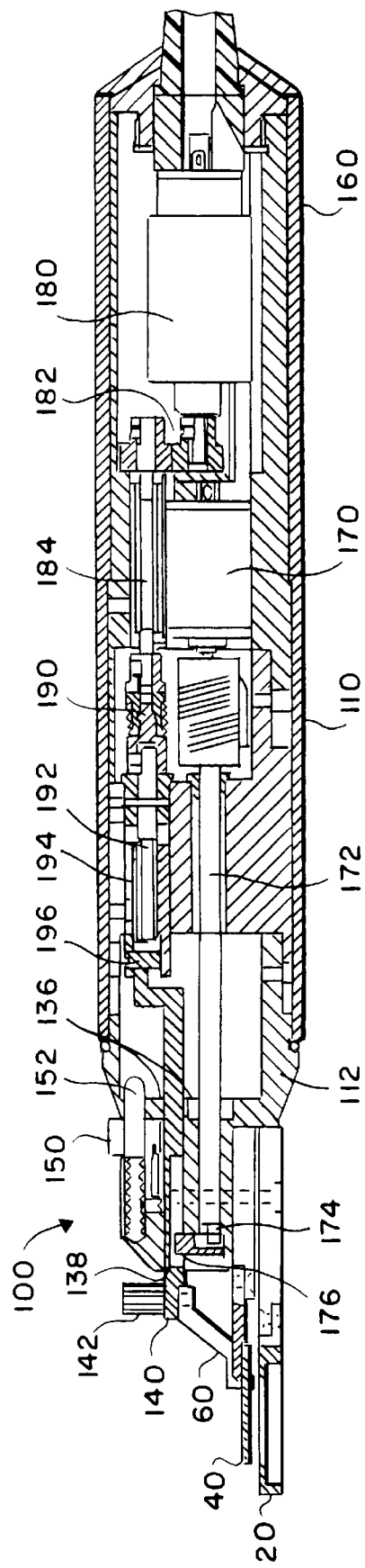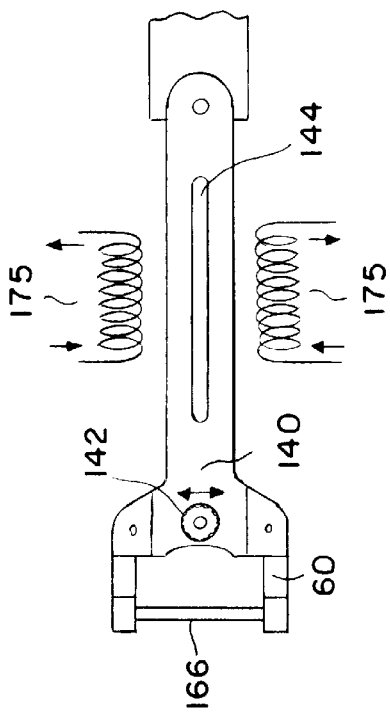

KERATOME METHOD AND APPARATUS

FIELD OF THE INVENTION

The present invention pertains to the general field of ophthalmologic surgical devices, and more specifically to the field of devices for performing corneal resectioning and methods therefor.

BACKGROUND

Numerous ophthalmic surgical procedures, such as for correcting myopia or hyperopia, require one or more steps of resectioning the cornea of the eye. A variety of devices called keratomes have been developed over recent decades to perform such corneal resectioning. Referring to FIGS. 1, 2a and 2b, a typical resectioning operation will separate flap 6 of corneal tissue 2 from eyeball 4. The tougher outer layers of epithelial cells 8 are separated and lifted away to expose the more compliant inner layers 12 of cornea 2, but the separated outer layers are left attached as flap 6. Once exposed, interior layers 12 of cornea 2 will to some extent adjust themselves, or their shape may be altered through further surgical steps. Such further steps may include, for example, making radial keratotomy cuts or performing a subsequent resectioning which may include removing a contoured layer of corneal tissue. At the conclusion of the various steps of the surgical procedure, flap 6 is typically replaced over inner corneal tissues 12 to protect the healing tissues.

The representative keratomes described in U.S. Pat. Nos. 5,496,339 issued to Koepnick, and Re. 35,421 issued to Ruiz et al., which are depicted in FIGS. 3a and 3b, demonstrate many standard features of prior art keratomes. A retaining ring for positioning and retaining the subject eyeball is typically supplied with a source of vacuum. The vacuum pressure draws the eyeball into the retaining ring so that the cornea protrudes through the retaining ring and presses against the surface of a feature, herein referred to as an applanation shoe, which is provided to restrain the protruding cornea. The applanation shoe is desirably made of transparent material to help the surgeon to position the cornea and to observe it during the surgery. A cutting blade is then drawn across the positioned cornea to a preset stopping point, desirably oscillating as it is moved forward. Both the thickness and the expanse of the corneal tissue which is cut must be carefully controlled. The separated portion of the cornea may be completely removed, but typically one edge of the sectioned layer is left attached to form flap 6 which can easily be replaced over the cornea after the surgery.

Keratomes must have a mechanism by which the knife blade is guided. Proximate to the cutting location, the prior art keratomes all have blades rubbing on guides, or metal rubbing on metal, such as drive gears. Unfortunately, such rubbing can result in shavings being created and entering the surgical site. Referring to FIG. 3a, the keratome of Ruiz et al. has an intricate mechanism with metal-on-metal gears rubbing in the surgical vicinity. For example, pinion 834 rides on track 891 which is part of positioning ring 890; and endless pinion 822, along with its eccentric shaft and associated pinions, operates directly above the blade cutting site (not shown). In FIG. 3b, the keratome of Koepnick is seen to have blade 954 which rubs directly on the insert 948 and slides in surfaces defined along line 991. The sliding surfaces at 991 are located directly above positioning suction ring 990, and the rubbing surface between blade 954 and insert 948 is directly adjacent regions of intimate contact between the corneal tissue and insert 948. Thus, these two prior art keratome examples have rubbing between the cutting blade and other surfaces, and rubbing of gears, very close to the surgical site.

Another drawback of existing keratomes is the inconvenience of maintaining surgical cleanliness. Since parts of the keratome must be in intimate contact with tissues around and including the surgical site, it is necessary to ensure a high degree of cleanliness and sterility. The relatively intricate mechanisms which prior art keratomes position near the surgical site, as described above, have not been well-adapted for ease of cleaning and autoclaving.

Thus, a need exists for an easily used keratome able to perform precise resectioning operations, while facilitating surgical cleanliness by avoiding creation of shavings which might contaminate the surgical site, and by being easily cleaned, sterilized, and replaced.

SUMMARY OF THE INVENTION

The present invention relates to a surgical device for enabling an ophthalmologic surgeon to perform corneal resectioning. In accordance with the present invention, the surgical device preferably includes a surgical unit having cutting head elements mounted on a drive assembly, and also includes a control unit and a footpedal. During surgery, the cutting head elements are in intimate contact with the subject eye, for positioning and cutting. The drive assembly element supports and drives the cutting head elements. The control unit is the preferred source of power and vacuum for the surgical unit, and it supplies power and vacuum according to settings entered by the user. The footpedal allows the user to give commands to the surgical device without requiring use of hands. The surgical unit is preferably hand-held and easily positioned over the subject eye.

The surgical unit includes four distinct elements. Three of these are "cutting head" elements which must contact the eye during corneal surgery—a positioning ring assembly, an applanation assembly, and a blade fork assembly. Each of these three cutting head elements extends from the fourth element, a drive assembly, in such a way that interference and rubbing between the cutting head elements proximal to the surgical site is minimal or entirely absent. Preferably, each of the three cutting head elements is easily removed and as easily replaced onto the fourth element, the drive assembly, so the surgeon can ensure sterility by simply snapping in fresh and sterile replacements for the three cutting head elements.

In accordance with the present invention, a blade fork assembly suspends a cutting blade between the positioning ring and the applanation shoe and guides the cutting blade near to the applanation shoe. The nature of the cut is preferably controlled in one of two ways: 1) the blade may be caused to travel in a plane which is a fixed distance away from the applanation shoe, thereby separating that portion of the cornea which lies between the plane of the blade and the applanation shoe; or 2), the blade fork assembly may include a guide suspended parallel to and a fixed distance from the blade, with the outer layer of corneal tissue separated as it passes between the blade and the guide so that the thickness of the separated layer is controlled by the spacing between the blade and the guide.

Preferably, the positioning ring assembly, the applanator assembly, and the blade fork assembly are removably attached to a handheld drive assembly. A further preferred feature of the present invention is a hinged applanator. Such an applanator may be swung out of the way while the eye is retained by the positioning ring, which permits examination and further surgical procedures to be performed on the subject cornea without a need to remove the surgical unit.

Of the three cutting head elements employed in the preferred embodiment of the present invention, only the blade fork assembly must move during resectioning. The blade fork assembly is caused to move by the drive assembly, which, through its blade fork drive arm, imparts two distinct movements to the blade fork assembly during cutting action: one movement is a high-speed lateral oscillation, and the other, imparted at the same time, is a slow smooth forward movement. The means by which the drive assembly actuates the drive arm is explained further in the drive assembly section below. The drive arm may continue to impel the blade fork forward as long as it is commanded to do so through the control unit, until the drive arm impinges on an adjustable stop mechanism. Thereafter, a clutch will slip to prevent further forward displacement of the drive arm.

In several embodiments, the blade assembly is entirely suspended and does not touch any part of the mechanism which is near to the surgical site except indirectly by way of the blade fork drive arm which supports it. In an alternate embodiment, however, a minimal amount of moving contact may occur between a guide near the blade and a surface of the applanation shoe.

BRIEF DESCRIPTION OF THE DRAWINGS

FIG. 10b shows a releasable locking method for the applanator of FIG. 10a.

FIG. 11b shows details of positioning ring restraint at section 11b—11b of FIG. 11a.

FIG. 12 shows a cross-section of a surgical unit using motor driven blade oscillation.

FIG. 13 shows alternative features for the surgical unit to permit field-driven blade oscillation.

DETAILED DESCRIPTION

Figure 1:
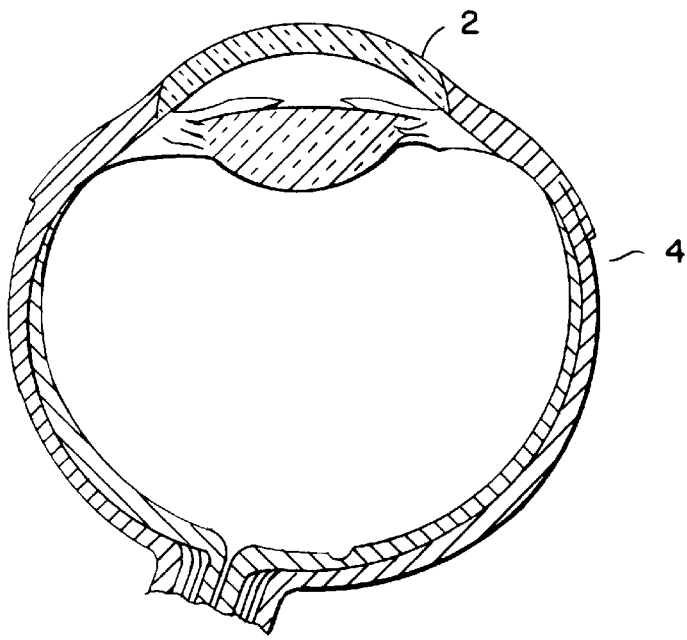
FIG. 1 is a cross-section of an eye.
Figure 2A:
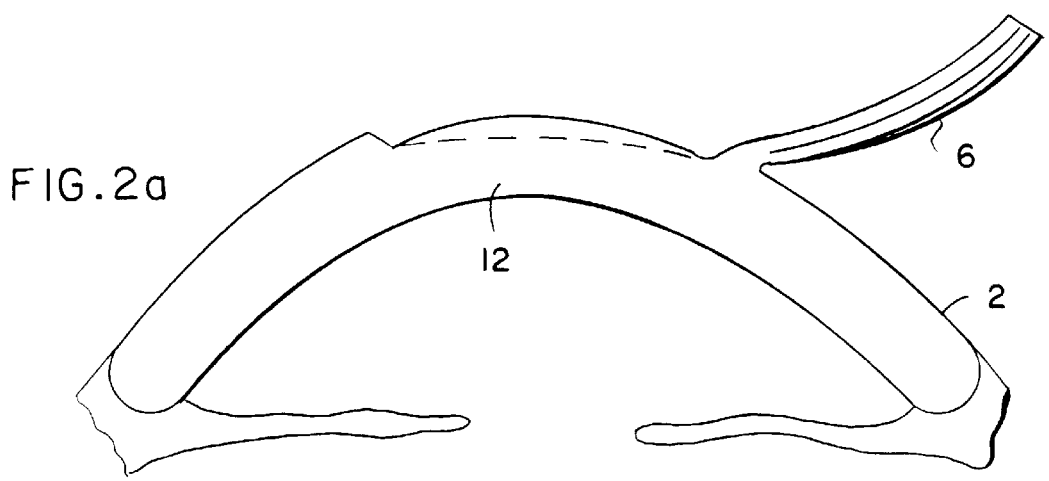
FIG. 2a shows a cornea with a flap of epithelial tissue lifted.
Figure 2B:
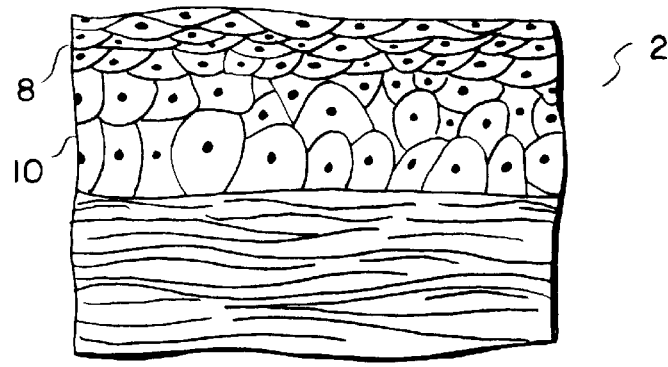
FIG. 2b is a representation of the variation of corneal tissue beginning at the outermost layers.
Figure 3A:
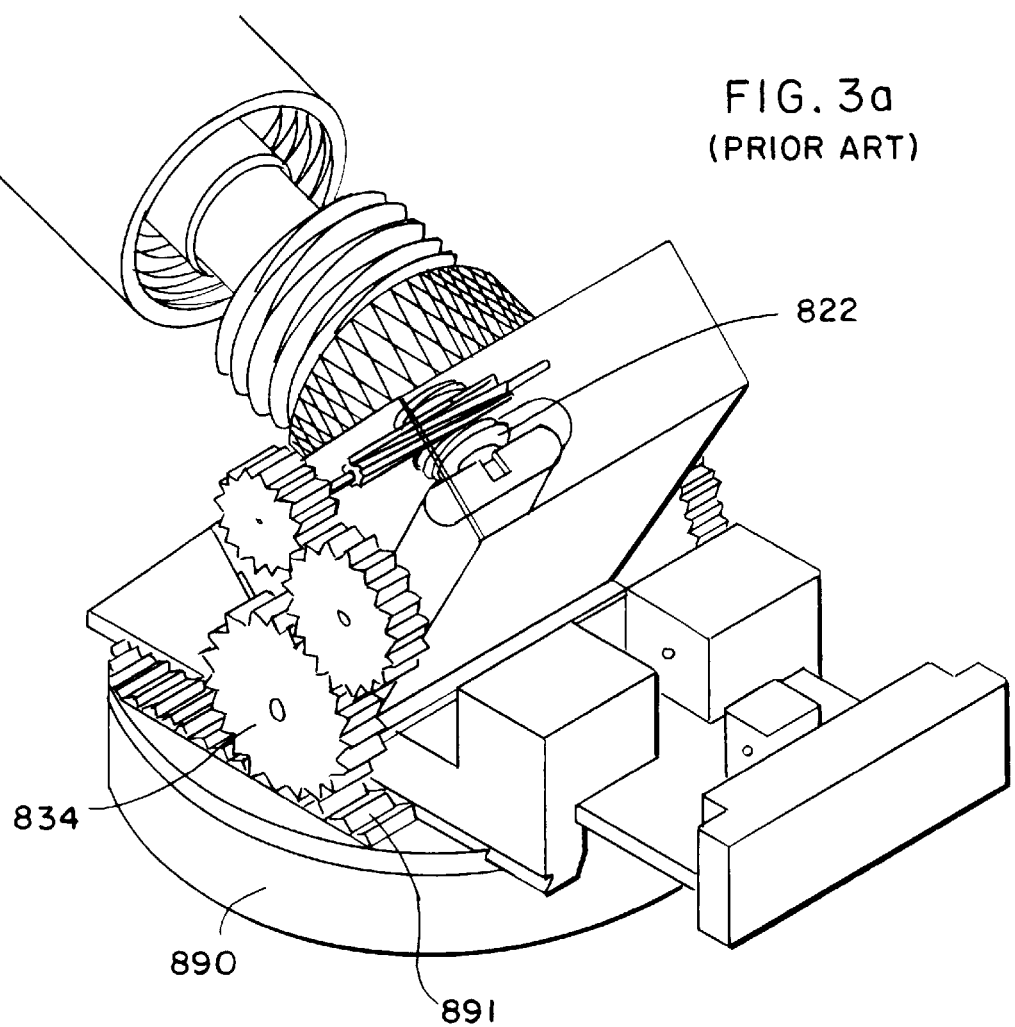
FIG. 3a shows the prior art keratome of Ruiz et al.
Figure 3B:
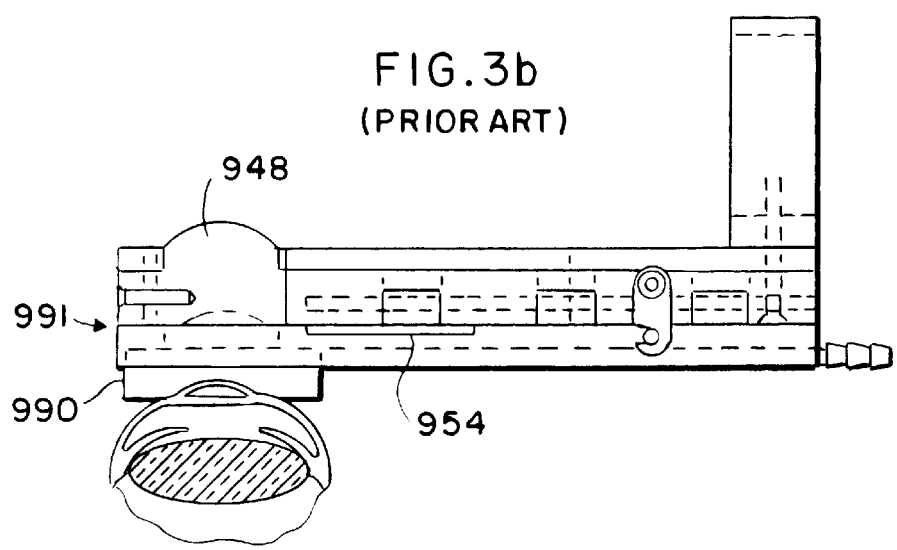
FIG. 3b shows the prior art keratome of Koepnick.
Figure 4:
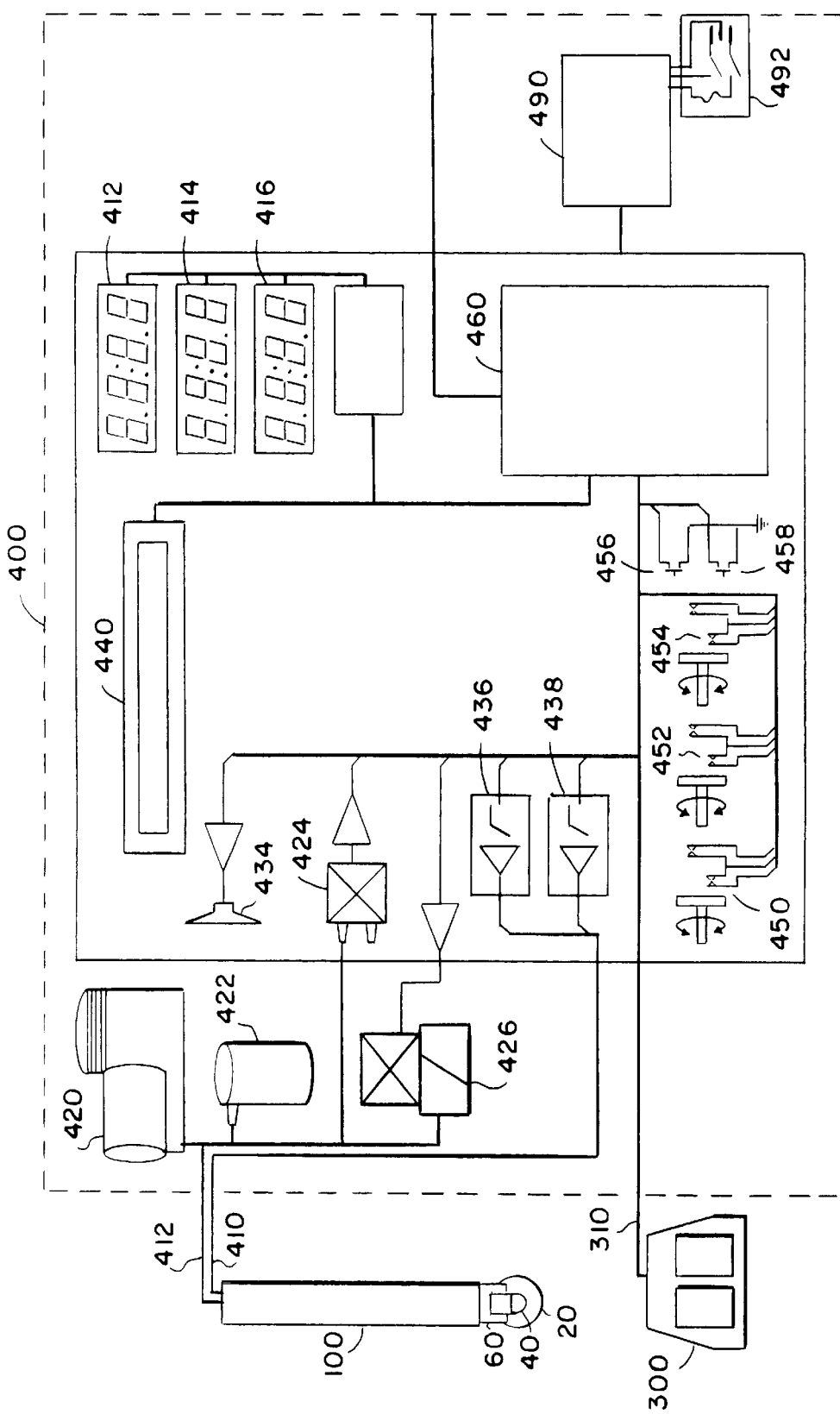
FIG. 4 shows the control unit with connections to the surgical unit and to a foot pedal.
Figure 5:
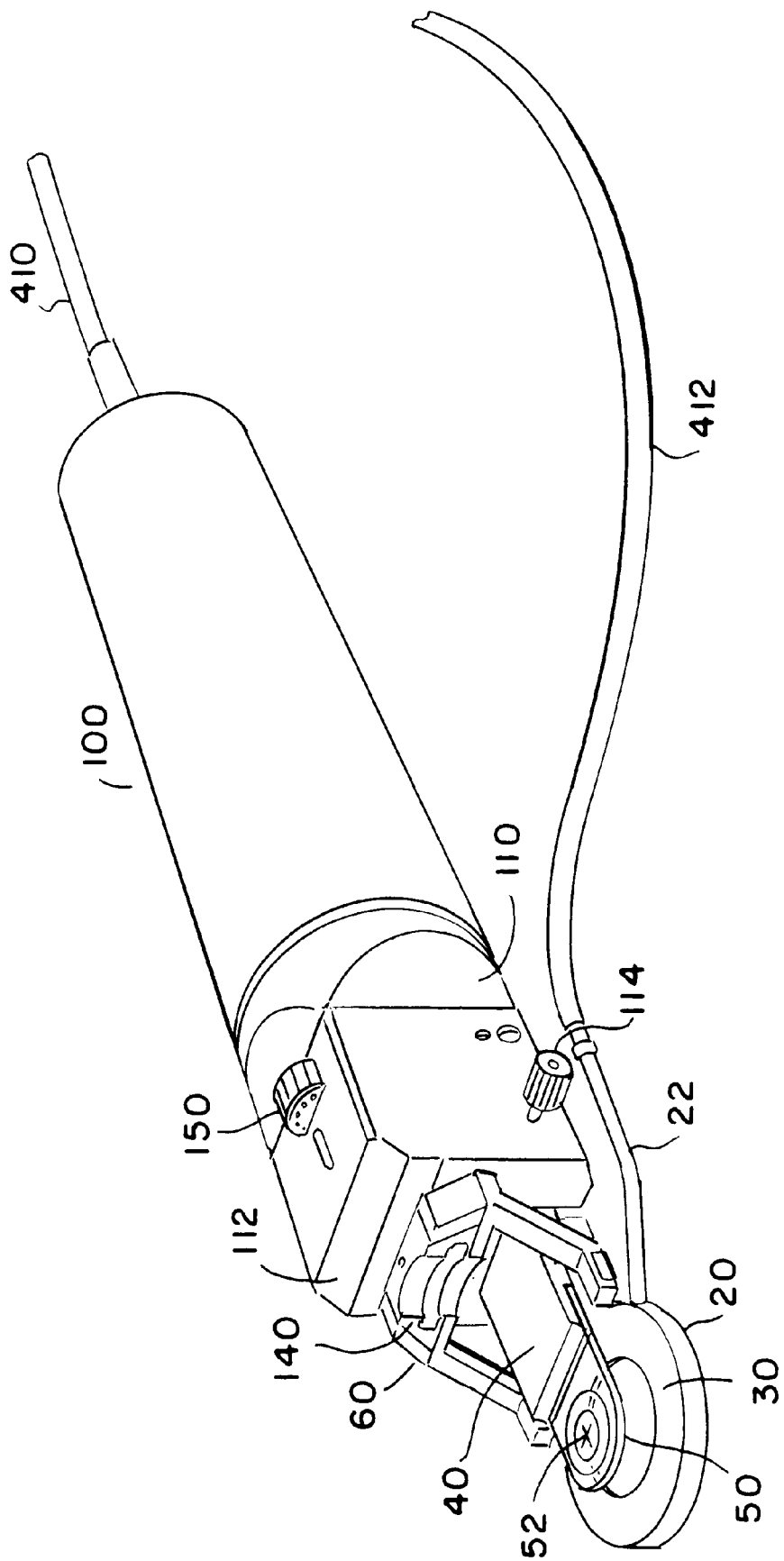
FIG. 5 shows the surgical unit, with the cutting head elements attached to the drive assembly.

Referring to FIGS. 4 & 5, the present invention is preferably embodied in three separate components: surgical unit 100, footpedal 300, and control unit 400. Surgical unit 100 has four subsections including drive assembly 110 and three cutting head elements: positioning ring assembly 20, applanator assembly 40, and blade fork assembly 60. Footpedal 300 communicates user commands to control unit 400 via cable 310, and surgical unit 100 is connected to control unit 400 by electrical cable 410 and vacuum hose 412. Each of these items are discussed in more detail below.

CONTROL UNIT

The following describes a preferred embodiment of the invention with reference to FIG. 4. Control unit 400 is a microprocessor-controlled unit enabling the user to direct operation of the actuators within drive assembly 10 and the level of vacuum supplied to positioning ring assembly 20 of surgical unit 100. The user controls operation by means of two pedal switches of footpedal 300, in conjunction with three rotary input devices 450, 452 and 454 and two pushbuttons 456 and 458 on the front panel of control unit 400. Operating parameters are displayed on the front panel for the user by means of numeric readouts 412, 414 and 416 and by multiple character alpha-numeric display 440, while speaker 434 gives audible information.

A microprocessor on printed circuit board 460 executes operating firmware which is held in reprogrammable non-volatile memory and can be reprogrammed in the field. The firmware allows the microprocessor system to read switch closures and the rotation of the rotary controls. These electronics translate operator actions into tool control voltages which are applied to the drive unit actuators and can be stored as presets to be recalled as required by the operator. The microprocessor system also interprets the sensors and controls the actuators to maintain vacuum at a level set by the user.

Control unit 400 provides electric control signals to surgical unit 100 via cable 410. Vacuum pressure for positioning ring assembly 20 is supplied from control unit 400 via vacuum hose 412. Control unit 400 contains vacuum reservoir 422 in which vacuum pressure is established by vacuum pump 420 and released by vacuum release solenoid 426, and the vacuum pressure is sensed by vacuum transducer 424 to give feedback to the control electronics.

Electric control for the actuators (not shown) within drive assembly 110 is provided by electronic switches 436–438. Persons skilled in the art will appreciate that there is no limit to the variations by which control unit components may control the surgical unit actuators and vacuum.

SURGICAL UNIT

Referring to FIG. 5, surgical unit 100 includes drive assembly 110 for supporting and driving three cutting head elements which contact the eye during surgery. The cutting head elements include positioning ring assembly 20, applanator assembly 40, and blade fork assembly 60. Surgical unit 100 is supplied electrically via cable 410, and vacuum is supplied to positioning ring 30 via vacuum hose 412 which attaches to vacuum connection tube 22.

Figure 6:
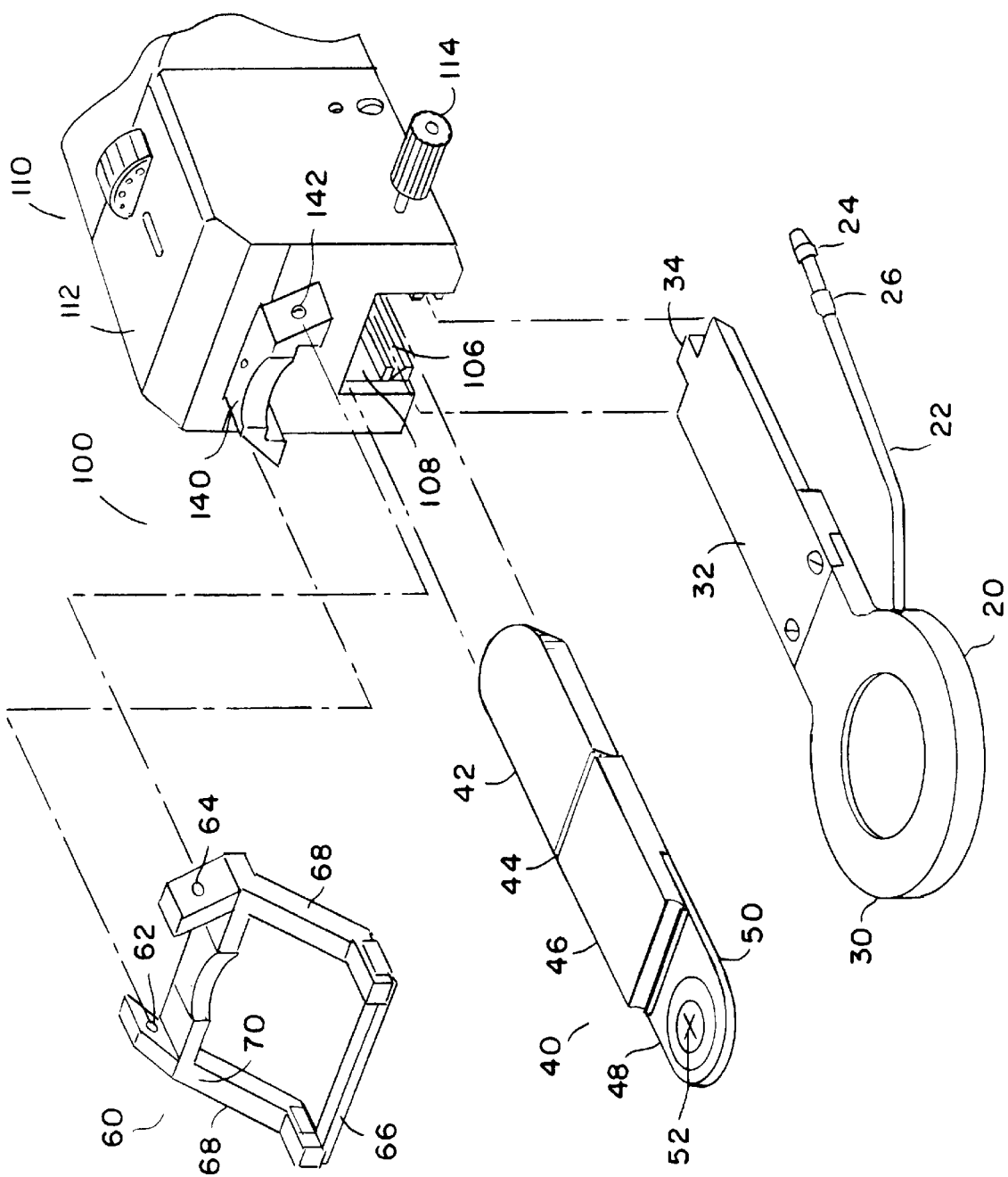
FIG. 6 shows the front of the drive assembly with the cutting head elements detached therefrom.

FIG. 6 clearly delineates the three cutting head elements, including positioning ring assembly 20, applanator assembly 40, and blade fork assembly 60, as they are separated from drive assembly 110. Since each of these cutting head elements ordinarily comes into direct contact with an eye being operated upon, it is preferable that they be easily removable from, and replaceable on, drive assembly 110, in order to facilitate the use of clean and sterile elements. For the same reason, it is also preferable that these cutting head elements be either sterilizable or sterile disposable. The four elements 20, 40, 60 and 110 of surgical unit 100 are each described in more detail below.

Surgical Cutting Action

FIGS. 7a–7d show the cutting head elements in use resectioning cornea 2. Vacuum pressure delivered to vacuum chamber 36 of positioning ring 30 will draw sclera 3 and cornea 2 of eye 4 upward such that cornea 2 is pressed against applanation shoe 50. In this first preferred embodiment, blade fork assembly 70 suspends blade 66 so the blade travels in a plane between positioning ring 30 and applanation shoe 50 but without contacting either ring 30 or shoe 50. Blade fork drive arm 140 (FIG. 5) supports the blade fork assembly and imparts a compound movement to it. Blade fork assembly 70 is oscillated rapidly in a direction parallel to the cutting edge of blade 66 (in and out of the page of FIGS. 7a–7d), and simultaneously moved slowly forward (from right to left in FIGS. 7a–7d), while maintaining blade 66 at a controlled distance from applanation shoe 50. Blade 66 thereby separates that layer of corneal tissue 2 which is positioned between the plane of travel of blade 66 and the near surface of applanation shoe 50. The forward travel of blade fork assembly 70 continues until the formation of flap 6 is completed.

Figure 7A:
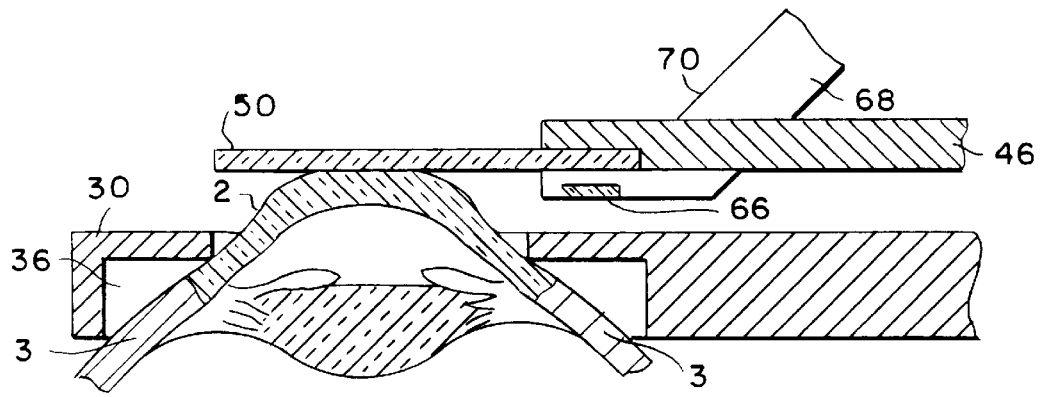
FIG. 7a shows an eyeball held against the applanator shoe by the positioning ring with a blade supported by the blade fork and prepared to initiate a cut.
Figure 7B:
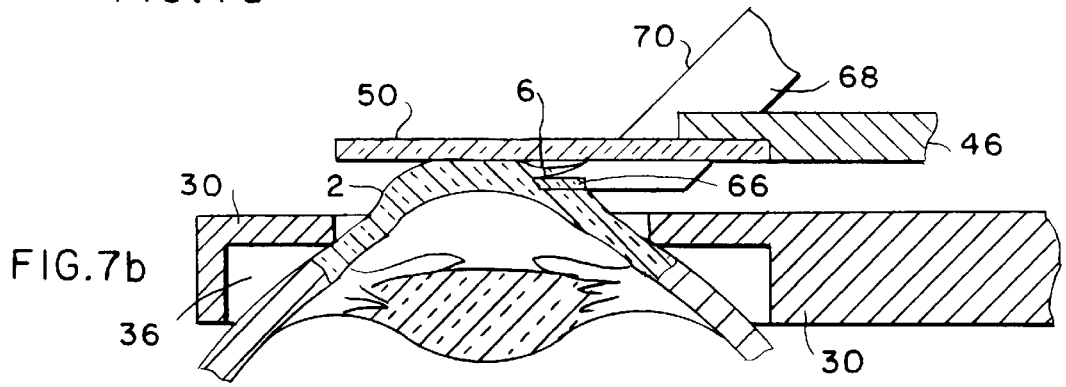
FIG. 7b shows the blade of 7a in process of completing a cut.
Figure 7C:
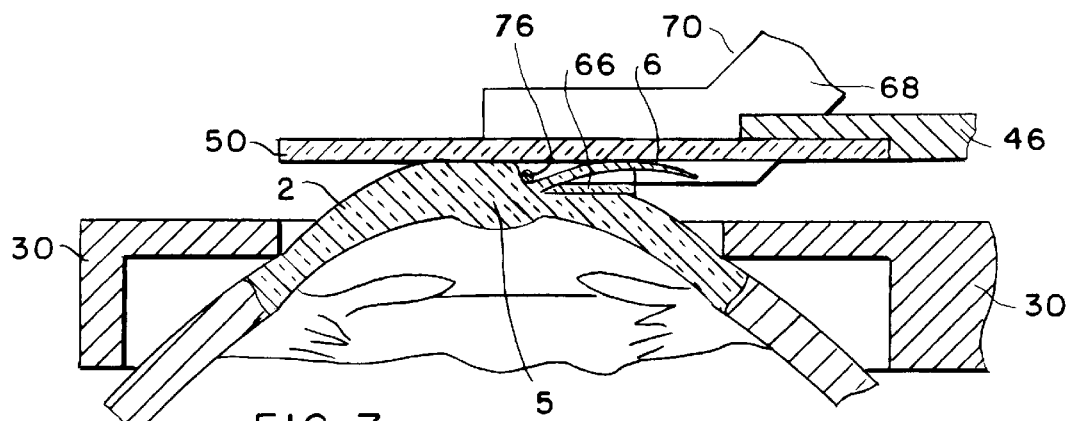
FIG. 7c shows a blade assembly using a guide to set the thickness of a cut.

FIG. 7c depicts a resectioning operation employing a second preferred embodiment of blade fork assembly 70. There, blade 66 and guide 76 are both suspended between tines 68 of blade fork assembly 70, as can be seen in FIG. 8c. Blade fork assembly 70 moves blade 66 and guide 76 in a plane near to applanation shoe 50, preferably maintaining clearance from the shoe, while performing the same simultaneous oscillating and forward cutting movements described above. As can be seen at location 5, cornea 2 deforms around guide 76 as the blade fork travels forward, with guide 76 preferably not contacting applanation shoe 50. As corneal flap 6 is separated from the rest of cornea 2 by blade 66, it must pass between blade 66 and guide 76. The thickness of flap 6 is thus controlled by the spacing set between blade 66 and guide 76 on blade fork assembly 70. Details of this embodiment of the arrangement of blade 66 and guide 76 on blade fork 70 are shown in FIG. 8d.

Figure 7D:
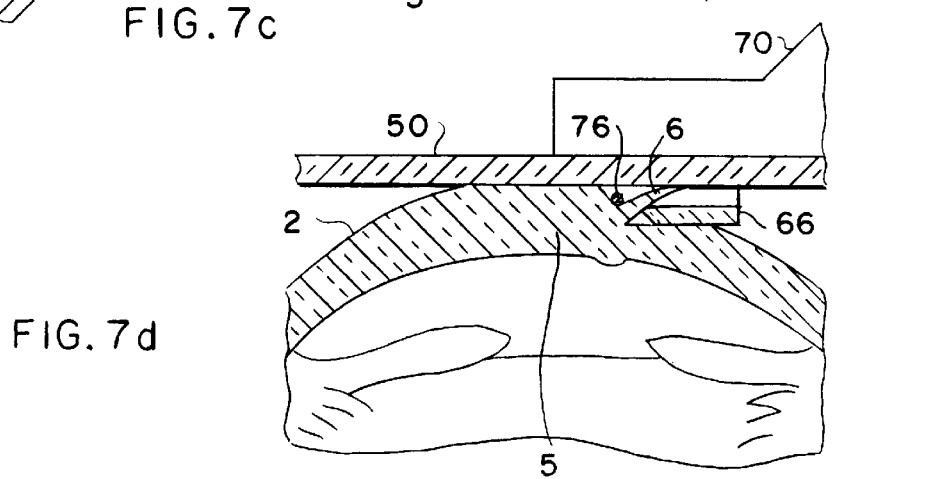
FIG. 7d shows cutting as in FIG. 7c but permitting the guide to contact the applanation shoe.

FIG. 7d shows resectioning action of a third embodiment of the present invention, very similar to that described above in reference to FIG. 7c. In FIG. 7d the thickness of corneal flap 6 is again controlled by the spacing set between guide 76 and blade 66. In accordance with this third embodiment, guide 76 may optionally be positioned less forward of blade 66 (in the direction of travel) than would be appropriate for the second embodiment above. In FIG. 7d, moreover, guide 76 may be in actual contact with applanation shoe 50, unlike in FIG. 7c. Details of this embodiment of blade fork assembly 70, at cross-section 8f—8f, are shown in FIG. 8f.

Blade Fork Assembly

Figure 8A:
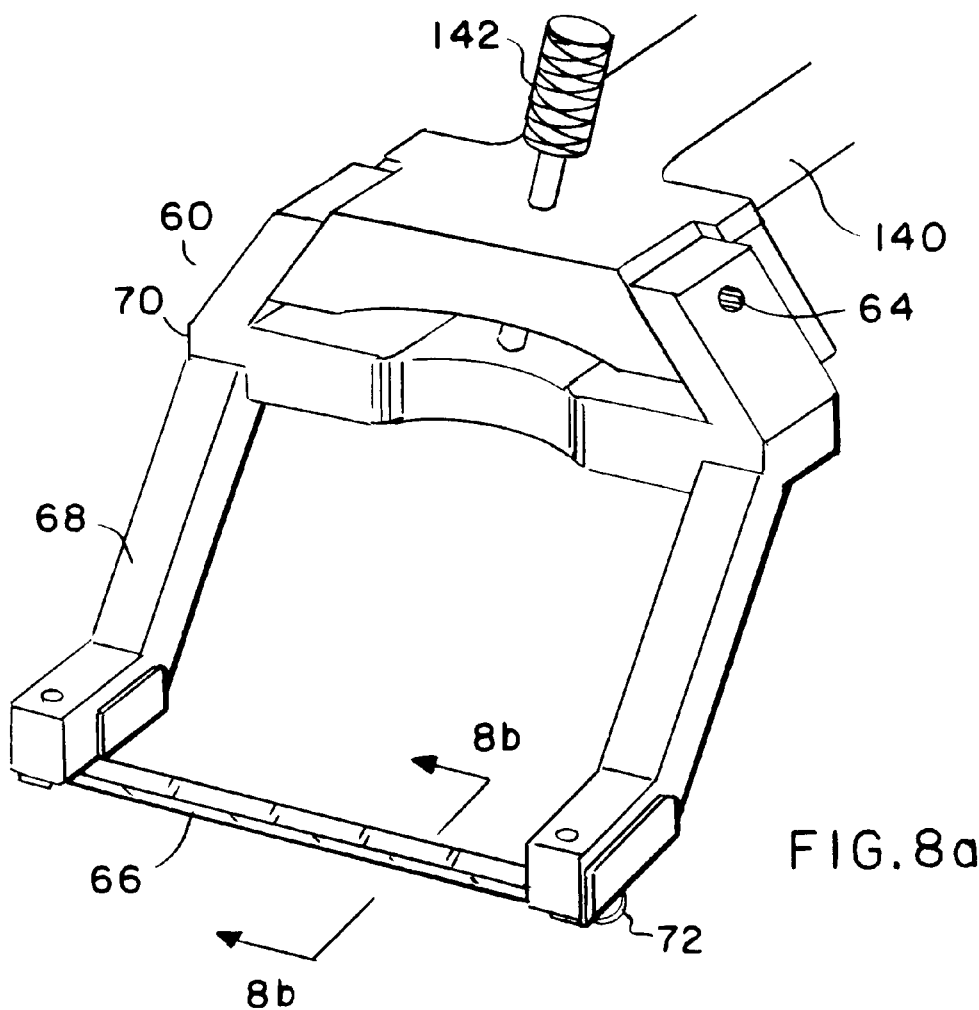
FIG. 8a shows a blade fork assembly with a thumb screw securing it to the blade fork drive arm.

FIG. 8a shows blade fork assembly 60 supporting blade 66 and connecting it to blade fork drive arm 140 which impels assembly 60. A dove-tail or trapezoidal attachment mechanism between blade fork 70 and blade fork drive arm 140 is shown. Threaded spring-ball assembly 64 in blade fork 70 causes a ball to press into a complementary detent, not shown, in drive arm 140 to properly position blade fork 70 to drive arm 140.

Blade fork 70 is preferably composed of titanium but many other materials are suitable, including stainless steel. For a steam sterilizable blade fork, dimensionally stable plastics such as polycarbonate or polysulfone are suitable, and gas or gamma ray sterilization is compatible with additional plastics, such as polypropylene.

Blade 66 is preferably sapphire or similar crystalline materials, which is hard and strong and desirably transparent for the best visibility as the cutting operation progresses. Alternatively, and particularly for disposable versions, the blade may be surgical stainless steel or other suitable material.

The overall position of blade 66 with respect to applanation shoe 50 is established by the combined positioning of blade 66 in blade fork assembly 60, by the relative positioning of drive arm 140 to applanator assembly 40 which is described later under "Drive Assembly," and by the position of applanation shoe 50 with respect to the position of the applanator assembly, described later under "Applanator Assembly." In the absence of guide 76, the position of blade 66 is preferably maintained within 0.050 mm, and even more preferably within 0.030 mm, of a selected distance from the surface reference plane of applanation shoe 50. In the presence of guide 76 this distance from blade 66 is preferably maintained within 0.5 mm and even more preferably within 0.1 mm or less, but tolerances even larger than 0.5 mm may be acceptable, particularly in embodiments in which guide 76 is permitted to contact applanation shoe 50.

In order to meet these overall positioning tolerances, in embodiments without guide 76, blade fork assembly 60 is preferably constructed to position blade 66 within 0.03 mm, and even more preferably within 0.015 mm of an intended plane known with respect to the surfaces where fork 70 attaches to drive arm 140. In use with guide 76, blade fork assembly 60 is preferably constructed to position blade 66 within 0.3 mm, or more preferably within 0.15 mm, of an intended plane known with respect to the surfaces where fork 70 attaches to drive arm 140. However, it is within the scope of the present invention to permit tolerances twice as large as those enumerated as preferred. Thumb screw 142 provides one preferred means to secure the attachment between blade fork 70 and drive arm 140.

Figure 8B:
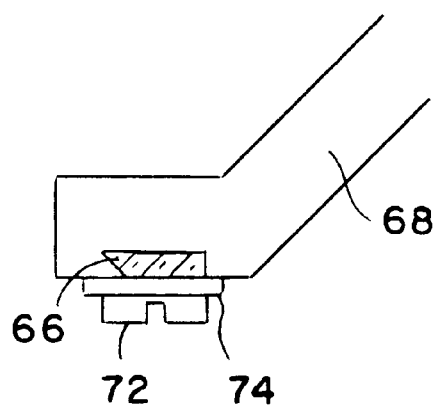
FIG. 8b shows details of a section 8b—8b of FIG. 8a, including the blade.
Figure 8C:
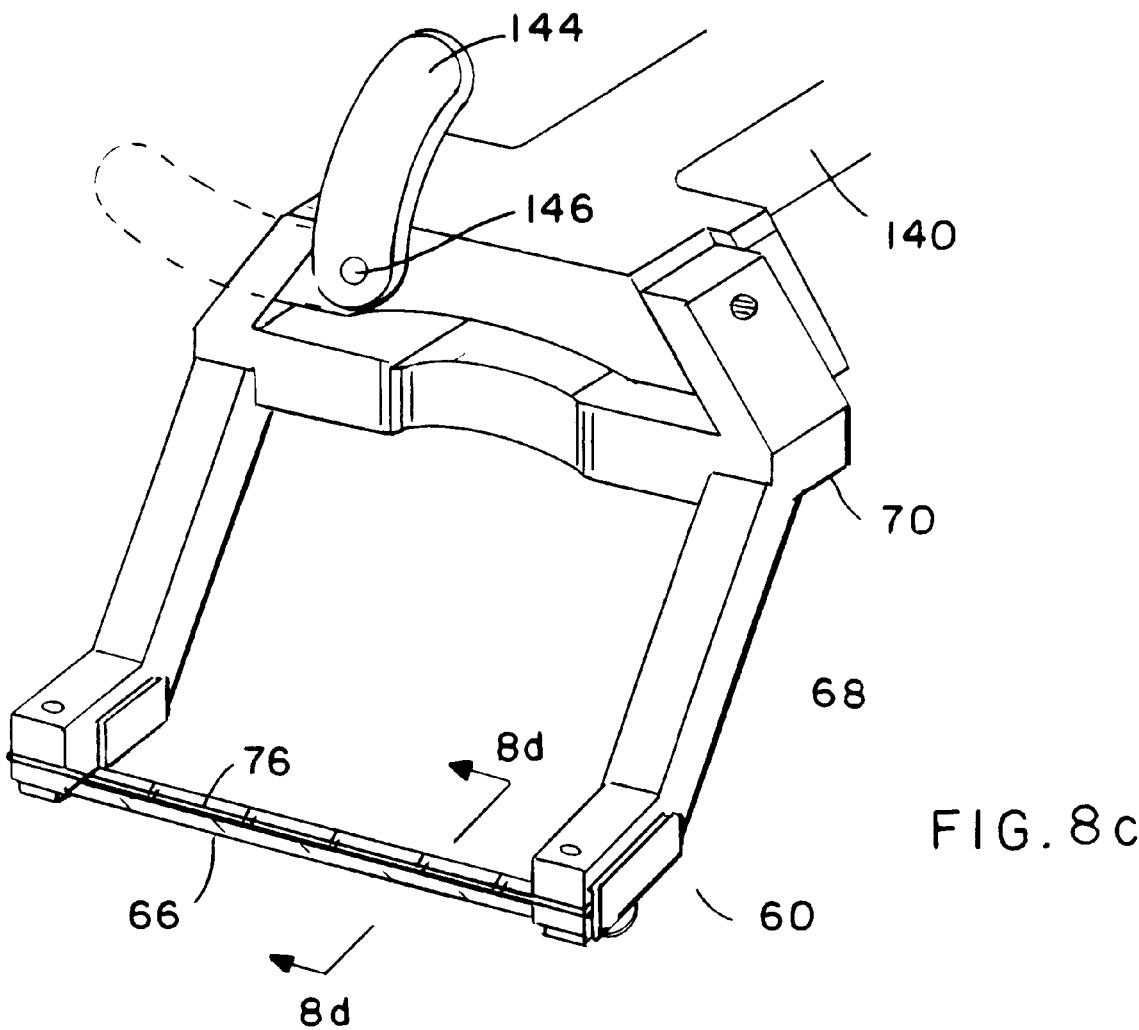
FIG. 8c shows a blade fork assembly with a cam lever securing it to the blade fork drive arm.
Figure 8D:
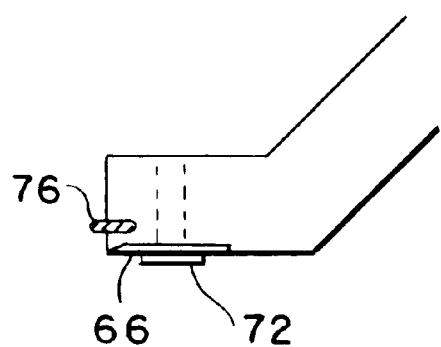
FIG. 8d shows details of section 8d—8d of FIG. 8c, including a stainless steel blade with guide.

FIG. 8b shows cross-section 8b—8b of FIG. 8a, including blade 66, retaining screw 72 and washer 74. According to this embodiment, the thickness of the layer of cornea cut depends upon the distance maintained between blade 66 and applanation shoe 50 (FIG. 6). One skilled in the art will appreciate that many other embodiments of blade fork assembly 60 which do not utilize guide 76 (FIGS. 8c–8h) are possible, including versions of FIGS. 8c–8f which omit guide 76.

FIG. 8c shows an embodiment of drive fork assembly 60 incorporating guide 76 disposed parallel to blade 66. The spacing between guide 76 and blade 66 controls the thickness of corneal tissue cut, enabling the cut thickness to be controlled very precisely and also to be set under controlled conditions at the factory. Guide 76 has a cross-section defined in a plane perpendicular to the longitudinal axis of blade 66.

The perimeter of the cross-section of guide 76 is advantageously small, preferably less than 2 mm or less than 6 mm. A small cross-sectional perimeter conveys several advantages: it reduces the frictional interaction between the guide and the cornea, it localizes a deformation of the cornea to avoid pressure on the eye generally, and it reduces the likelihood of trapped bubbles distorting the cornea to cause inaccurate cuts.

FIG. 8c also shows a second means for securing the trapezoidal attachment between blade fork 70 and drive arm 140, the means comprising locking lever 144 which actuates a locking cam (not shown) by rotating about pivot 146.

FIG. 8d shows cross-section 8d—8d of FIG. 8c, including stainless steel blade 66 and guide 76, preferably of polished stainless steel, and rivet 72.

Alternative embodiments of the present invention may differently employ embodiments of blade fork assembly 60 incorporating guide 76 (FIGS. 8c–8h). In one embodiment guide 76 may be permitted, and in another embodiment not be permitted, to contact the applanation shoe.

Figure 8E:
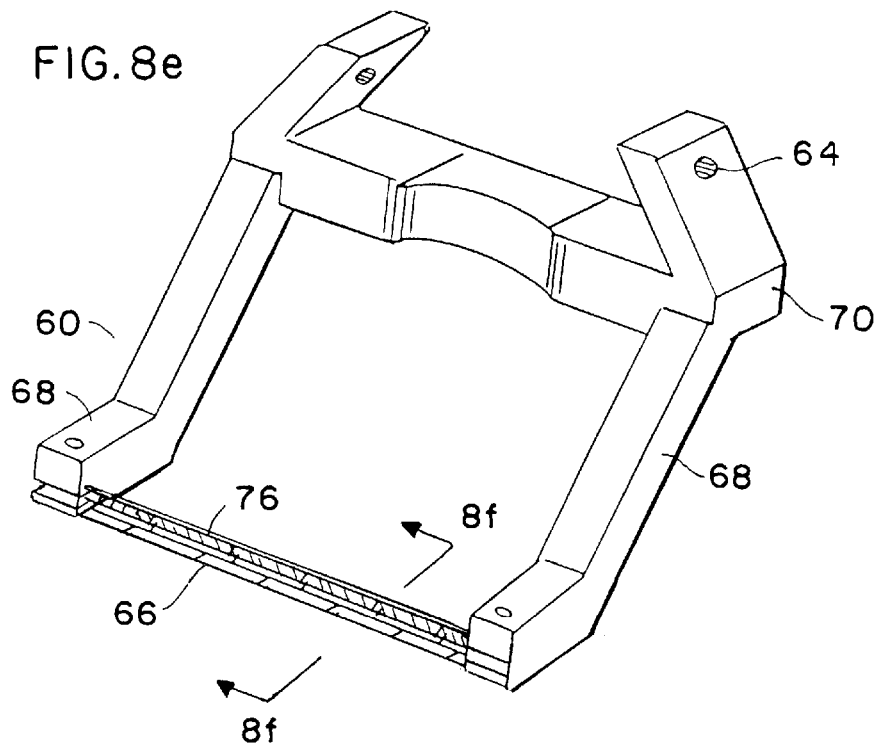
FIG. 8e shows a blade fork assembly with a particular arrangement of blade and guide.

FIG. 8e shows another embodiment of blade fork assembly 60. Cross-section 8f—8f of blade fork assembly 60 is shown in FIG. 8f. The leading edge of guide 76 is positioned very slightly forward (in the direction that the cutting head elements extend from the drive assembly) of the cutting edge of blade 66. Dimension x 1 is the distance in the direction of blade travel between the leading edge of blade 66 and the leading edge of guide 76. The optimum length of dimension x1 depends on the orientations of the plane of blade 66 and, if applicable, of guide 76. Dimension x1 is preferably greater than zero, for example 0.20+/−0.05 mm or 0.30+/−0.05 mm. Dimension y1, the distance between guide 76 and blade 66 in a direction perpendicular to the travel plane of blade 66, will vary depending upon the surgeon's needs, but will typically be made nominally 0.150 mm, 0.160 mm, 0.170 mm, or 0.180 mm, each nominal dimension being controlled to within a tolerance of preferably 0.030 mm or even more preferably 0.015 mm.

With any embodiment of blade fork assembly incorporating guide 76, clearance may be maintained between guide 76 and the applanation shoe during cutting, or else guide 76 may be allowed to touch the applanation shoe; the latter condition is shown in FIG. 7d.

Figure 8I:
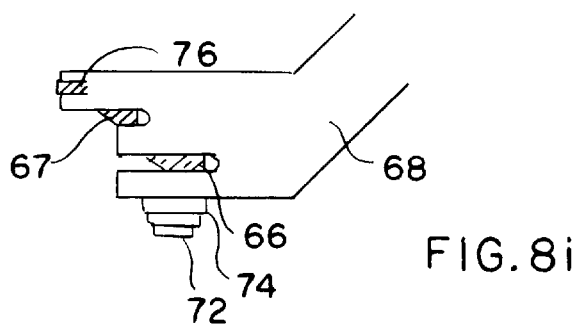
FIG. 8i shows details of a blade fork assembly including dual blades.
Figure 8F:
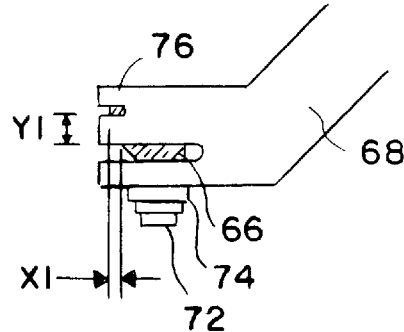
FIG. 8f shows detail of section 8f—8f of FIG. 8e.
Figure 8G:
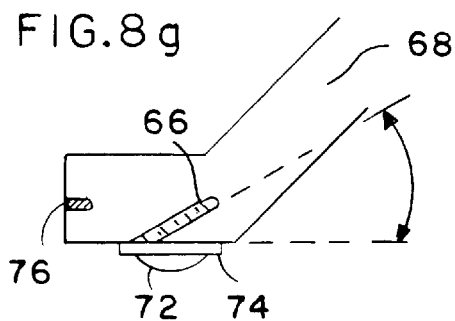
FIG. 8g shows a view similar to section 8f—8f with an alternative arrangement of blade and guide.
Figure 8H:
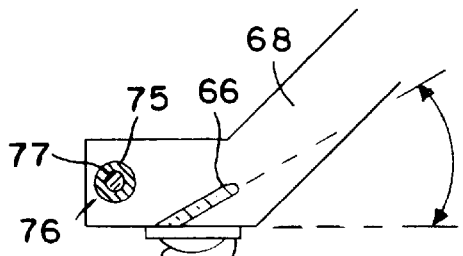
FIG. 8h shows details similar to 8g with the guide having a rolling bearing cover.

FIGS. 8g and 8h are cross-sectional views emphasizing the cross-sectional shapes of blade 66 and guide 76. They are similar to cross-sectional view 8f—8f of FIG. 8f, but they depict alternative blade fork assemblies. In FIG. 8g, blade 66 is shown having a small angle to the direction of travel, the angle preferably being about 25 degrees. FIG. 8h differs from FIG. 8g in that guide 76 comprises central core 75 and outer cylindrical bearing 77, which is preferably made of a tough, low friction material such as a plastic containing TEFLON(™) material.

FIG. 8i shows a cross-section similar to those described above of the blade fork, blade and attachment details. In FIG. 8i, two blades are shown, blade 66 and blade 67, in addition to guide 76. According to this embodiment, a single cutting pass of the blade assembly will enable the user to remove a slice of corneal tissue of precise dimensions, thus permitting insertion of surgical implants, while leaving flap 6 to cover the surgical site. The use of blades 66 and 67 together may also be practiced in the absence of guide 76.

Applanator Assembly

Referring to FIGS. 5, 6, 9a, 9b and 10a, applanation shoe 50 is that part of applanator assembly 40 which includes the surface for restraining the cornea during resectioning operations. Applanator assembly 40 includes applanator retention insert 42, hinge 44, applanation shoe support 46, and applanation shoe 50. Applanation shoe 50 is preferably made of a transparent and abrasion-resistant material such as glass or sapphire, and marked with crosshairs 52, to make the cutting operation visible to the surgeon. If the applanator is not hinged, then insert 42 and support 46 may be subparts of the same part.

Figure 11A:
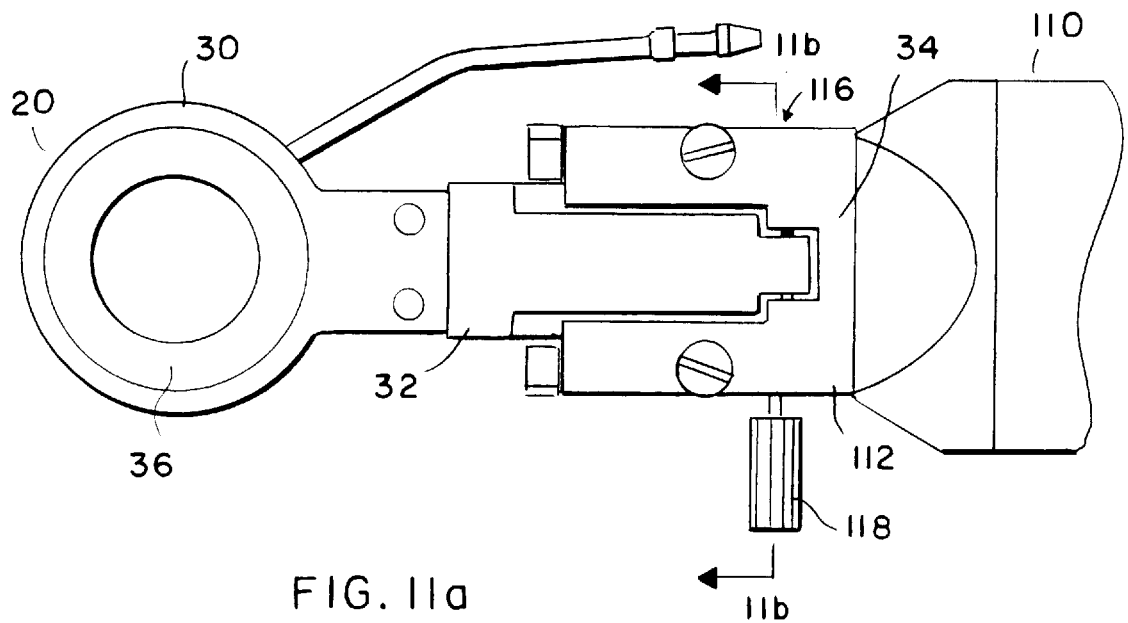
FIG. 11a shows the positioning ring attached to the drive assembly.
Figure 11B:
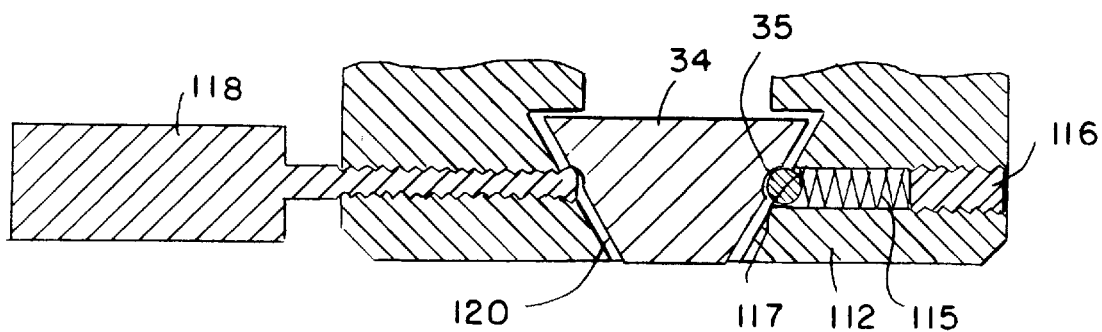

Applanator retention insert 42 and shoe support 46 preferably have trapezoidal edges, and slide into mating recess 108 of drive assembly 110, where they are located by a threaded captive-ball spring assembly on one side, and secured by thumbscrew 114 on the other side, in a manner similar to that described below in regard to positioning ring retention feature 34 of positioning ring assembly 20 (FIG. 11b).

As discussed above with respect to blade fork assembly 60, various materials may be used to construct applanator retention insert 42, applanation shoe support 46, and applanation shoe 50. For versions in which a guide 76 does not contact applanation shoe 50, abrasion resistance is less important. As above, the material chosen must be compatible with the method to be used to assure sterility of the element, whether a method such as heat, steam, gas, or gamma is used, or the element is sterile disposable. All of the same materials as for blade fork assembly 60 may be used, including preferably clear materials for applanation shoe 50.

Figure 9A:
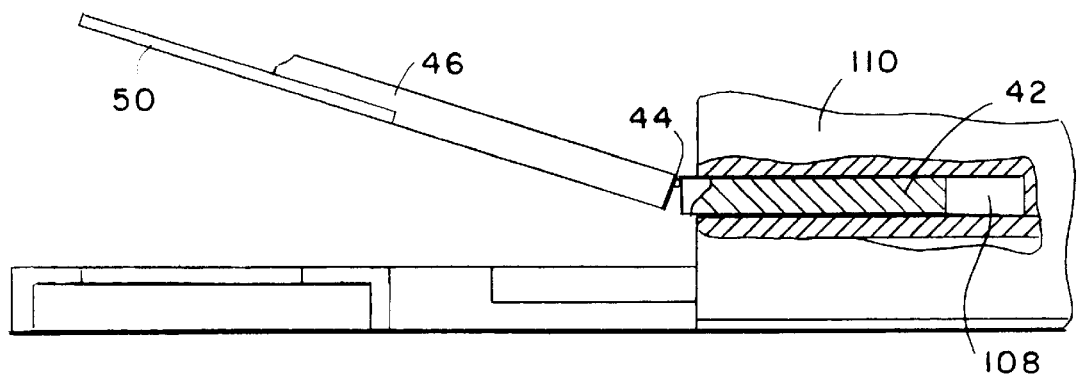
FIG. 9a shows an applanator extended and swung up and away from the positioning ring.
Figure 9B:
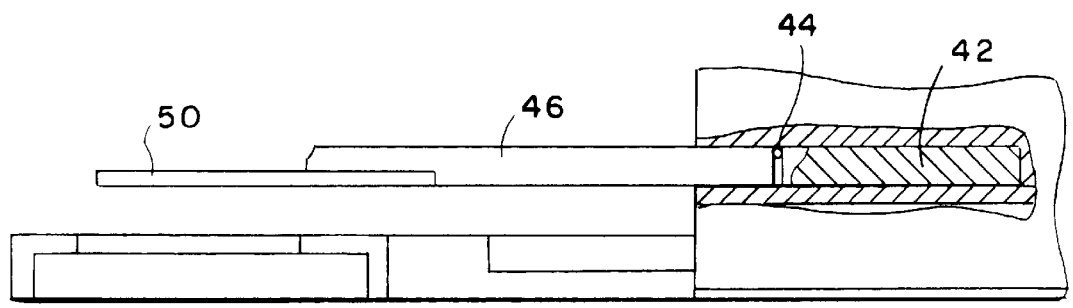
FIG. 9b shows the same applanator in the fully restrained position.

Applanator assembly 40 is preferably able to swing out of the way to expose the cornea of an eyeball held in the retaining ring 30. One preferred mechanism to permit such swinging is shown in FIGS. 9a and 9b. In FIG. 9a, applanator assembly 40 is partly withdrawn from recess 108 in drive assembly 110 into which it is mounted, so that hinge 44 is exposed and applanation shoe 50, along with support 46, is enabled to swing up, preferably about 60 degrees, relative to applanator retention insert 42 which remains in recess 108. In FIG. 9b, applanator assembly 40 is fully home so that hinge 44 is captive in recess 108. Applanator assembly 40 is secured to drive assembly 110 by thumbscrew 114, which impinges on applanator retention insert 42.

Figure 10A:
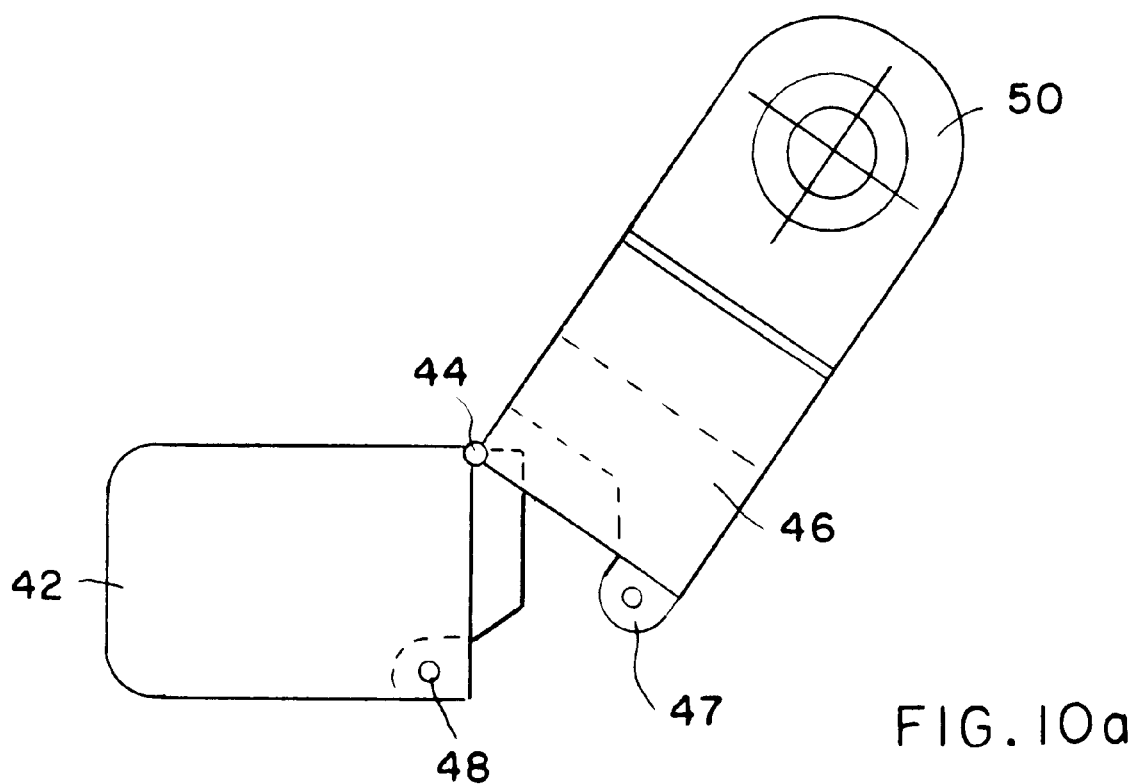
FIG. 10a shows an alternative method of swinging the applanator away.
Figure 10B:
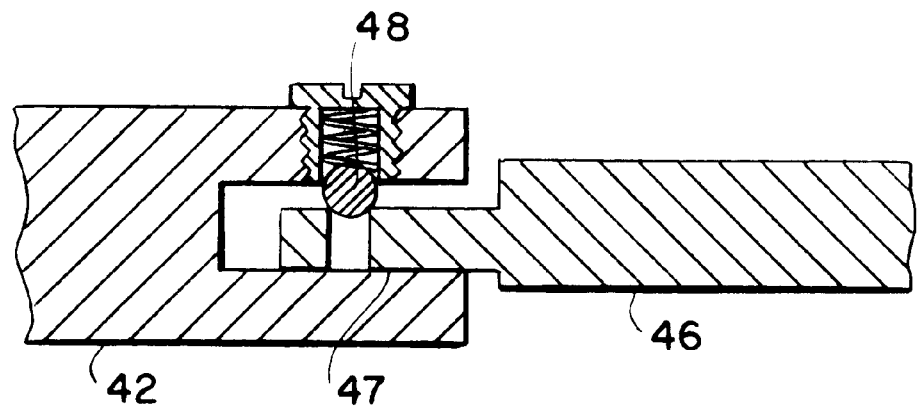

A second preferred embodiment to enable swinging is shown in FIG. 10a. There, hinge 44 permits applanation shoe 50 and support 46 to pivot away from applanator retention insert 42 while remaining in the same plane as insert 42. FIG. 10a shows shoe 50 with support 46 pivoted away from applanator retention insert 42, exposing latch feature 47. When closed, latch feature 47 will engage spring ball 48, thereby releasably securing the applanator in the closed position. FIG. 10b shows a cross-sectional detail of engaged latching mechanism 48.

A different contour of applanation shoe 50 may be used for different stages of resectioning by simply replacing the applanator. Accordingly, the corneal restraining surface of applanation shoe 50 may be perfectly flat, or it may be contoured. Since the blade must be guided a controlled distance from the applanation shoe, in the case of a contoured surface for applanation shoe 50 it is useful to define a "surface reference plane." Such a plane is the reference according to which the blade travel is guided.

Conceptually, the applanation shoe surface reference plane is the plane which "just touches" the corneal restraint surface, and which is parallel to the desired cutting plane. The surface reference plane is defined at the time the contour of the applanation shoe is designed, and functions as the reference to which positioning and tolerances between the blade travel and the applanation shoe are established and maintained.

Blade travel is controlled with respect to the surface reference plane of the applanator. In embodiments not utilizing guide 76, the applanator is preferably constructed such that the applanation shoe reference plane is everywhere within 0.030 mm, and even more preferably within 0.015 mm, of a plane known precisely relative to the mounting surfaces of the applanator mounting bracket. However, in other embodiments of the present invention, for example when blade fork assembly 60 includes guide 76, the applanator may be constructed so that the applanation shoe reference plane is everywhere within 0.5 mm, or more preferably 0.2 mm, of a plane known precisely relative to the mounting surfaces of the applanator mounting bracket.

Referring now to FIG. 7b, as blade 66 separates that part of cornea 2 which is positioned between the cutting plane of blade 66 and applanation shoe 50, flap 6 of corneal tissue created by the cutting of the blade will reflect the sum of the contouring of applanation shoe 50 plus the distance between the travel plane of blade 66 and the applanation shoe reference plane.

Positioning Ring Assembly

FIGS. 11a and 11b depicts details of positioning ring assembly 20. Positioning ring 30 is provided with vacuum to vacuum chamber 36 so that an eyeball placed against it may be drawn in, distending the cornea which is then typically pressed against applanation shoe 50 as shown in FIGS. 7a–7d. The vacuum is furnished through vacuum connection tube 22, with the vacuum hose (not shown) placed over vacuum connection nipple 24 and stopped by vacuum tube stop 26. Alternatively, vacuum could be ducted through ring support 32 and drive assembly 110 to obviate vacuum connection tube 22, the vacuum hose connected then only to drive assembly 110.

Referring to FIG. 11a, which is a bottom view, and cross-section FIG. 11b, positioning ring support 32 preferably includes retention feature 34 having detent 35. Retention feature 34 slides into matching recess 120 in drive assembly 110. Captured ball 117 settles into detent 35 under the pressure of captured spring 115 to properly locate positioning ring assembly 20. Then, thumbscrew 118 secures retention feature 34, seating it firmly against the sides of recess 120 formed in head 112 of drive assembly 110. (Note that FIG. 11a omits thumbscrew 114, located in head 112 opposite thumbscrew 118, and used for securing the applanation assembly.)

As discussed with regard to blade fork assembly 60 and applanator 40, a variety of materials may be used for positioning ring 20. The choice depends on whether sterility is to be ensured by reuse of the element in conjunction with a sterilization method, or by using sterile disposable elements. Suitable materials include metals, such as stainless steel, and plastics, such as polycarbonate, polysulfone, polypropylene or others.

Drive Assembly

FIGS. 12 & 13 show details of a preferred embodiment for surgical unit 100, and in particular shows details of a preferred embodiment for drive assembly 110, which is largely enclosed by drive assembly cover 160.

Referring to FIG. 12, the primary actuators within drive assembly 110 are travel motor 180 and oscillation motor 170. Travel motor 180 drives shaft 184 through gear train 182. Clutch 190 couples a limited torque to screw 192. The rotational motion of screw 192 is converted to linear motion by threaded traveller 194. Pivot assembly 196 couples the motion from the forward end of traveller 194 to blade fork drive arm 140, while permitting drive arm 140 to oscillate rotationally about the pivot of pivot assembly 196. Blade travel stop adjust knob 150 preferably rotates a threaded member which adjustably stops blade fork drive arm 140 travel.

Drive arm 140 preferably includes portions of its top and bottom surface which are made closely parallel to each other and a controlled distance apart (the top and bottom surfaces are those most distal from the center of drive arm 140 in the direction parallel to the pivot axis of pivot assembly 196, with the top surface being the farther from positioning ring 30). Drive arm 140 top and bottom surfaces are preferably flat to within 0.005 mm over their travel range of 1.5 cm, and are slidably captured by bearing surfaces 136 and 138 of drive assembly head 112. The bearing surfaces limit top-to-bottom play of drive arm 140 to preferably 0.01 mm or even more preferably to 0.05 mm.

Drive assembly head 112 holds applanator assembly 40 and blade fork drive arm 140 such that blade 66 is maintained a known distance away from applanation shoe 50 as it travels, as described above in the section entitled "Blade Fork Assembly." The tolerances needed to establish precise relative positioning between the drive arm and the applanator mounting surface are preferably established by either placing shims, or by machining head 112 (see FIGS. 5, 6). This procedure may adjust either the position of bearing surfaces 136, 138 for drive arm 140, or the position of recess 108 for applanator assembly 40. Control of the actual blade travel and applanation shoe reference planes then further depends on the precise construction of those cutting head elements, discussed in their respective sections above. In embodiments utilizing guide 76 (not shown) parallel to blade 66 on blade fork 70, the distance between blade 66 and applanation shoe 50 is preferably controlled to within +/−0.5 mm, or more preferably within +/−0.25 mm.

Oscillation is imparted to drive arm 140 by slider 176 which oscillates in a direction perpendicular to the page. Slider 176 interferes with the edges of a groove in drive arm 140, while the groove allows drive arm 140 to travel in and out of drive assembly 110. Slider 176 receives oscillation drive from oscillation motor 170 via shaft 172 and eccentric pin 174. Eccentric pin 174 rides in a slot in slider 176 which absorbs the vertical component of eccentric pin 174, but transmits the lateral motion.

ALTERNATIVE EMBODIMENTS OF THE INVENTION

It will be appreciated by those skilled in the art that many alternative embodiments are envisioned within the scope of the present invention. Some possible variations of the blade fork assembly are discussed in the blade fork assembly section above. Variations of other parts are discussed below, but do not represent an exhaustive survey of possibilities; rather, they serve as examples to show that a wide variety of mechanisms are encompassed within the scope of the invention.

FIG. 13 shows an alternative embodiment of means to impart oscillating motion to drive arm 140. In this embodiment drive arm 140 incorporates ferromagnetic material 144 which is acted on by magnetic fields generated by coils 175 positioned along the sides of drive arm 140.

Myriad physical configurations of the connection interface surfaces which removably attach the blade fork assembly to the blade fork drive arm can provide the predictable positioning needed to practice the invention. The mating parts of the interface are described herein as trapezoidal or "dove-tail" but may take any form having locating features, including sawtooth, rectangular, eccentric oval, keyhole, or other shapes too numerous to enumerate.

Similarly, the means for securing the connection interface is shown herein as either a thumbscrew or a cam locking lever, but could be accomplished many other ways. To mention just a few examples, the mating parts could use magnetic attraction, spring-loaded detents, or tapered engaging pieces fitted into a recess formed partly from each of the mating parts. The mating pieces could even interfere snugly under normal conditions, and have a means to temporarily change the shape of one of the pieces to release the interference and thereby permit connecting or separating the interface. Any method known in the art to disengageably secure two pieces in a closely predictable relationship could be used.

A preferred embodiment of the applanator includes a pivot so the applanator can be pivoted away from the cornea. Hinges and pivots of all known types are well within the scope of this invention. A flexible chain, cable, strap or string could retain the applanation shoe when the rigid attachment is disconnected; or the applanator could be made retractable into the mechanism which supports it.

Any blade fork can be used which is able to suspend the blade, and the guide if used, in a well-controlled position with respect to the mounting surface of the connection interface. The blade and the guide may take a multitude of shapes and comprise a multitude of materials, a few of which alternatives are discussed herein.

A preferred embodiment of this invention includes sterile disposable or sterilizable disposable cutting head elements. A non-limiting variety of material choices suitable for such an embodiment is discussed above with respect to each cutting head element. There is no need for the various cutting head elements to be all disposable or all permanent, but a mixture of types is also suitable.

Surgical unit actuators may be driven by any known method, including pneumatic drive methods.

User commands may be recognized in any known way, including voice command reception, and sensing user activation of sensors or switches located on the surgical unit or in other convenient places. The commands thus recognized may exert control through any combination of control elements, which may include mechanical means, direct electrical control, or intelligent electrical control with intelligence provided by any means known to the art. The command recognition and control elements could be physically located any accessible place, and as an example could be placed largely or entirely within the surgical unit.

What is claimed is:

1. A surgical device for performing corneal resectioning, comprising:
    a positioning ring to position and retain an eyeball, the positioning ring having an opening for a cornea of the eyeball to protrude therethrough;
    an applanation shoe having a surface for restraining corneal tissue, the surface having a surface reference plane;
    a blade assembly including a blade having a cutting edge and a longitudinal axis parallel to the cutting edge, and a blade support mechanism attaching to the blade at attachment points near longitudinally distal ends of the blade to suspend the blade between the attachment points; and
    a drive mechanism holding the applanation shoe proximate the positioning ring such that a cornea protruding through the opening of the positioning ring presses against the restraining surface of the applanation shoe, the drive mechanism impelling the blade support mechanism to move the blade through a blade plane between the positioning ring and the applanation shoe at a controlled distance from the surface reference plane of the applanation shoe.

2. The surgical device of claim 1 wherein the drive mechanism supports the blade assembly to keep the blade assembly separated both from the applanation shoe and from the positioning ring while the drive mechanism impels the blade assembly.

3. The surgical device of claim 1 wherein the blade assembly includes a guide disposed at a constant distance from the blade cutting edge, the guide having a cross-sectional area defined in a plane perpendicular to the blade longitudinal axis, the cross-sectional area having a perimeter.

4. The surgical device of claim 3 wherein the perimeter of the guide is less than 6 mm.

5. The surgical device of claim 2 wherein the blade assembly includes a guide disposed at a constant distance from the blade cutting edge, the guide having a cross-sectional area defined in a plane perpendicular to the blade longitudinal axis, the cross-sectional area having a perimeter.

6. The surgical device of claim 5 wherein the perimeter of the guide is less than 6 mm.

7. The surgical device of claim 3 wherein the guide includes a core oriented parallel to the blade longitudinal axis and a bearing sheath annular to the core and rotatable thereabout.

8. A surgical device according to claim 1, wherein the applanation shoe is pivotably attached to a mounting bracket which is removably attachable to the drive mechanism.

9. A surgical device according to claim 1 wherein the applanation shoe surface is non-planar.

10. An applanator for restraining a cornea during corneal resectioning performed using a surgical device according to claim 1, said applanator comprising:
    the applanation shoe of claim 1; and
    a mounting bracket removably attachable to the surgical device;
    the surface reference plane of the applanation shoe having a precisely controlled positional relationship to mounting surfaces of the mounting bracket.

11. The applanator of claim 10 wherein the applanator is constructed to be sterile disposable.

12. The applanator of claim 10 wherein said mounting bracket attaches pivotably to the applanation shoe.

13. The applanator of claim 10, wherein the applanation shoe surface for restraining corneal tissue is non-planar.

14. The blade assembly for use with the surgical device according to claim 1 for performing corneal resectioning, the blade assembly comprising:
    a drive connection interface for removably connecting the blade assembly as a unit to a drive assembly of the surgical device;
    a blade as claimed in claim 1; and
    a support assembly having blade mountings which are connected to the blade at the blade attachment points to suspend the blade therebetween.

15. The blade assembly of claim 14 wherein the blade is transparent.

16. A blade assembly according to claim 14, further comprising a guide suspended parallel to the cutting edge of the blade at a controlled distance from the cutting edge, the guide having a cross-sectional area defined in a plane perpendicular to the blade longitudinal axis.

17. A blade assembly according to claim 16 wherein the guide includes a core and a bearing sheath, the bearing sheath annular to at least a portion of the core and rotating thereabout.

18. A blade assembly according to claim 14 wherein the blade cutting edge is sapphire.

19. The blade assembly of claim 14 wherein the guide perimeter is less than 6 mm and the blade assembly is disposable.

20. The blade assembly of claim 14 further comprising a second blade parallel to the first blade.

21. The blade assembly of claim 20 further comprising a guide suspended parallel to the cutting edge of the first blade at a controlled distance from a cutting edge of the first blade.

22. The blade for use with a surgical device according to claim 1 for performing corneal resectioning, the blade comprising:
   a cutting edge and a longitudinal axis parallel to the cutting edge; and
   blade attachment points proximate only to longitudinally distal ends of the blade for attachment to the blade support mechanism of the surgical device.

23. The blade of claim 22 wherein the cutting edge is transparent crystalline material.

24. The positioning ring for use with a surgical device according to claim 1 for performing corneal resectioning, the positioning ring comprising:
   a vacuum duct for connecting to a source of vacuum; and
   a ring having a vacuum chamber connected to the vacuum duct for applying the vacuum to a cornea and sclera of an eye to draw the eye into position for resectioning;
   the positioning ring bring removable from the surgical device by a user upon releasing securing features.

25. The positioning ring of claim 24 wherein the positioning ring is disposable.

26. A method for making a device for resectioning a cornea of an eye, the method comprising steps of:
   providing an eye positioning mechanism to position and retain an eyeball to cause a cornea of a positioned eyeball to protrude;
   providing a cornea restraint surface to restrain the protruded cornea of the positioned eyeball, the restraint surface having a surface reference plane;
   suspending a blade having a cutting edge and a longitudinal axis parallel to the cutting edge between blade attachment points located proximate to longitudinally distal ends of the blade by means of a blade support device, the blade support device and the blade forming a blade assembly;
   supporting the blade support device, the eye positioning mechanism, and the cornea restraint surface to position the blade between the eye positioning mechanism and the cornea restraint surface reference plane by means of a drive support assembly;
   providing an impelling mechanism to impel the blade through a traversal path at a controlled distance from the restraint surface reference plane; and
   providing controlling signals subject to commands of a user to control the impelling mechanism.

27. The method of claim 26 wherein the drive support assembly impels the blade assembly while supporting the blade assembly to maintain non-zero clearance between the blade assembly and both the positioning means and the cornea restraint surface.

28. The method of claim 27 wherein the blade assembly traversal path is maintained within +/−0.05 mm of a predetermined distance from the cornea restraint surface reference plane.

29. The method of claim 26 comprising the further step of suspending a guide a fixed distance from the blade such that corneal tissue must pass between the guide and the blade, thereby controlling the thickness of the corneal tissue which is cut.

30. The method of claim 26 wherein the step of providing a cornea restraint surface includes attaching the cornea restraint surface to the drive support assembly with a pivotable attachment whereby the cornea restraint surface pivots away from the cornea.

31. A method for making a blade support assembly for use with a device made according to claim 26 for surgically resectioning an eye, the method comprising the steps of:
   providing a drive connection interface for removably connecting the blade assembly as a unit to the drive support assembly of the surgical device;
   providing the blade, which has a cutting edge with a longitudinal axis parallel to the cutting edge and attachment points near longitudinally distal ends of the blade;
   suspending the blade between supports attached to the drive connection interface by attaching the blade to the supports at the blade attachment points.

32. The method of making a blade support assembly according to claim 31 comprising the further step of providing a guide suspended parallel to the cutting edge of the blade at a controlled distance from the cutting edge, the guide having a cross-sectional area defined in a plane perpendicular to the blade longitudinal axis, the cross-sectional area having a perimeter not longer than 10 mm.

33. The method of making a blade support assembly according to claim 31 wherein the blade support assembly is sterile disposable.

34. A method for making an applanator for use with a surgical device made according to the method of claim 26 for performing corneal resectioning, the method comprising the steps of:
   providing a mounting bracket for removably mounting the applanator to the drive support assembly of the surgical device;
   providing the cornea restraint surface of claim 26 having a surface for restraining corneal tissue, the surface having a cornea restraint surface reference plane; and
   positioning an applanation shoe such that the cornea restraint surface reference plane is precisely located with respect to.

35. A method for making an applanator according to claim 34 wherein the applanator is disposable.

* * * * *